United States Patent [19]

Wong et al.

[11] Patent Number: 5,618,687

[45] Date of Patent: Apr. 8, 1997

[54] PRODUCTION OF 7-AMINO CEPHALOSPORANIC ACID WITH D-AMINO OXIDASE AND DEACYLASE

[75] Inventors: Bing L. Wong, Lexington; Yong Q. Shen, Medford, both of Mass.

[73] Assignee: Biopure Corporation, Cambridge, Mass.

[21] Appl. No.: 333,623

[22] Filed: Nov. 2, 1994

Related U.S. Application Data

[63] Continuation of Ser. No. 184,773, Jan. 21, 1994, abandoned, which is a continuation of Ser. No. 873,596, Apr. 21, 1992, abandoned, which is a continuation of Ser. No. 333,546, Apr. 4, 1989, abandoned.

[51] Int. Cl.⁶ .............................. C12P 35/00; C12N 9/79
[52] U.S. Cl. .............................. 435/47; 435/227; 435/197
[58] Field of Search .............................. 435/47, 227, 197, 435/911

[56] References Cited

U.S. PATENT DOCUMENTS

| | | | |
|---|---|---|---|
| 3,239,394 | 3/1966 | Walton | 435/189 |
| 3,658,649 | 4/1972 | Arnold et al. | 435/47 |
| 3,682,777 | 8/1972 | Nara | 435/830 |
| 3,725,400 | 4/1973 | Voser | 435/47 |
| 3,776,815 | 12/1973 | Treichler et al. | 435/47 |
| 3,821,209 | 6/1974 | Arnold et al. | 435/47 |
| 3,960,662 | 6/1976 | Matsuda | 435/47 |
| 4,113,941 | 9/1978 | Huper et al. | 435/47 |
| 4,145,539 | 3/1979 | Hattori et al. | 435/47 |
| 4,774,179 | 9/1988 | Ichikawa et al. | 435/51 |

FOREIGN PATENT DOCUMENTS

| | | | |
|---|---|---|---|
| 0283218 | 9/1988 | European Pat. Off. . | |
| 0322032 | 6/1989 | European Pat. Off. | 435/51 |

OTHER PUBLICATIONS

ATCC Catalogue of bacteria, 1989, pp. 4–7.
Berg and Rodden, *Analytical Biochemistry* 71:214–222 (1976).

*Primary Examiner*—Irene Marx
*Attorney, Agent, or Firm*—Hamilton, Brook, Smith & Reynolds, P.C.

[57] ABSTRACT

An enzymatic process for the production of 7-amino cephalosporanic acid from cephalosporine C is disclosed. The process is a two-stage enzymatic reaction which can be performed in a single reactor. The invention further includes a mutant strain of *Trigonopsis variabilis* which produces increased amounts of D-amino acid oxidase, and a mutant strain of *Acinetobacter sp.*, which increased amounts of deacylase, which are enzymes necessary for the present process.

8 Claims, 1 Drawing Sheet

The Lineage of Improved Strain of *Trigonopsis variabilis*.
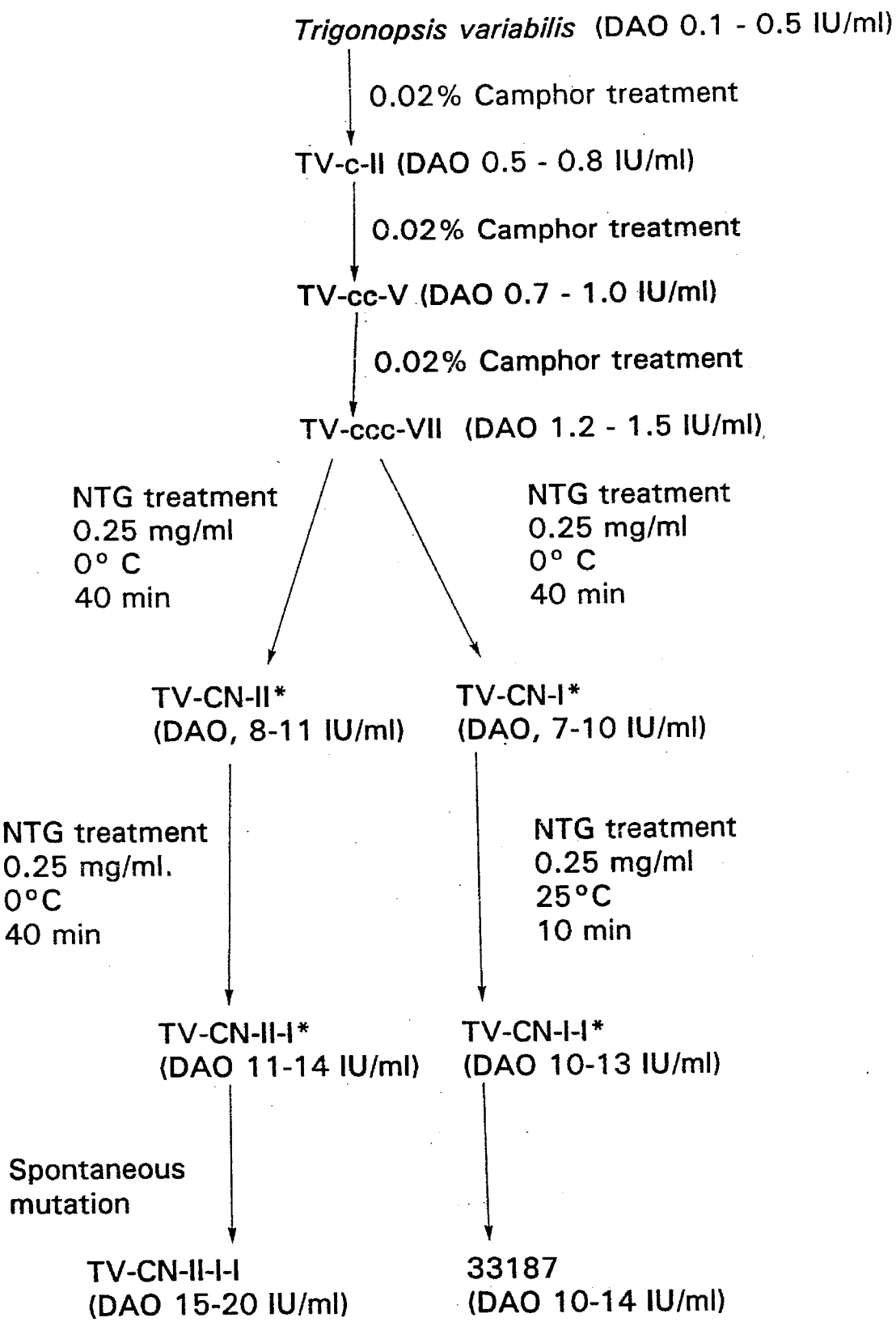

PRODUCTION OF 7-AMINO CEPHALOSPORANIC ACID WITH D-AMINO OXIDASE AND DEACYLASE

This application is a continuation of application Ser. No. 08/184,773 filed Jan. 21, 1994 (now abandoned), which is a File Wrapper Continuation of Ser. No. 07/873,596, filed Apr. 21, 1992 (now abandoned), which is a File Wrapper Continuation of Ser. No. 07/333,546, filed Apr. 4, 1989 (now abandoned).

BACKGROUND

Many organisms produce chemical substances that are toxic to other organisms. An important class of these compounds are medicinal antibiotics produced by yeast, fungi and bacteria, such as penicillin and streptomycin.

A major class of antibiotics is the cephalosporins. Cephalosporins, such as cephalosporin C and its derivatives, including 7-amino cephalosporanic acid, are important antibiotics. Methods of preparing cephalosporin C and its derivatives have been described, for example in U.S. Pat. No. 3,821,209; U.S. Pat. No. 3,658,649; U.S. Pat. No. 4,113,941; U.S. Pat. No. 3,776,815; U.S. Pat. No. 3,725,400; U.S. Pat. No. 4,145,539 and U.S. Pat. No. 3,960,662. However, better and more efficient methods for preparing cephalosporins are needed.

SUMMARY OF THE INVENTION

The present invention is a fully integrated process for the enzymatic production of 7-amino cephalosporanic acid from cephalosporin C, and related compounds. The process is a two step enzymatic reaction. The first step involves contacting cephalosporin C with an enzyme mixture comprising catalase and D-amino acid oxidase (DAO) to produce an intermediate, glutaryl 7-amino acid cephalosporanic acid. The second step involves contacting the acylated product with a deacylating enzyme, thereby producing 7-amino cephalosporanic acid in high yield. The reaction is carried out under a pressurized oxygen atmosphere, thereby allowing both steps of the reaction to be carried out in a single reaction vessel.

The invention also relates to a mutant strain of yeast, which produces large quantities of D-amino acid oxidase, and a mutant strain of bacteria which produces large quantities of deacylating enzyme. The preferred mutant is a strain of *Trigonopsis variabilis*, which expresses D-amino acid oxidase at a level about 160 times greater than wild type strains. The mutant yeast cells can be utilized in the present process for production of 7-amino cephalosporanic acid. The preferred mutant bacteria is a strain of *Acinetobacter sp.*, which expresses deacylating enzyme at a significantly higher level than the wild type strain.

The present process provides an efficient, single-vessel system for conversion of cephalosporin C to 7-amino cephalosporanic acid.

BRIEF DESCRIPTION OF THE FIGURE

The FIGURE depicts a flow chart showing the lineage of the improved strain of *T. variabilis*.

DETAILED DESCRIPTION OF THE INVENTION

The production of 7-amino cephalosporanic acid from cephalosporin C is a two-step enzymatic reaction: (1) the first step involves contacting cephalosporin C with a mixture of catalase and DAO to produce glutaryl 7-amino cephalosporanic acid (glutaryl-7ACA); (2) the second step involves contacting glutaryl 7ACA with a deacylating enzyme to produce 7-ACA.

In general, in prior processes the first enzyme step produces a reaction mixture: glutaryl 7ACA and a δ-ketoacid intermediate with glutaryl 7ACA as the predominant product. However, the δ-ketoacid intermediate reacts poorly with the deacylating enzyme. To improve the reactivity, an additional chemical reaction has been employed: a trace amount of hydrogen peroxide was introduced to the first enzymatic reaction mixture and the hydrogen peroxide reacts with the D-ketoacid product non-enzymatically in an oxidative decarboxylation. As a result, glutaryl 7-ACA is formed, and, the overall reaction takes place and is driven to completion.

The reaction solution is then introduced into a second enzyme reactor, which contains the deacylating enzyme, forming 7-ACA. However, before the second step can be performed, the hydrogen peroxide must be removed. The reaction solution must be exposed to a catalase enzyme to remove the hydrogen peroxide.

The present process eliminates the need for hydrogen peroxide, thus, the entire reaction can be performed in one reaction vessel. This is made possible because in the present system, the first enzyme reactor is operating under an oxygen atmosphere of about 50 psig, or higher, and glutaryl 7-ACA becomes the dominant product. Therefore, the steps of adding hydrogen peroxide to the reactor effluent and then removing the excess hydrogen peroxide with a catalase reactor can be eliminated. Under an optimal operating condition for both enzymes (e.g., 25° C., pH 8.0 and under 50 psig pressure) and suitable dissolved oxygen required by D-amino acid oxidase, the present process allows these two enzyme reactors to be interacted into a single unit to and thus achieve a single step conversion of Cephalosporin C to 7-ACA. (See Example 8)

ENZYMES

The enzymes used in the present process are DAO, catalase and a deacylating enzyme specific for glutaric acid.

DAO can be found in several sources, such as molds (e.g., *Penicillium chrysogenum, Penicillium roqueforti, Aspergillus niger, Neurospora crassa*), bacteria (e.g., *Aerobacter sp., Bacillus proteus, Pseudomonas aeruginosa*) yeast, (e.g., *Trigonopsis variabilis, Candid tropicalis, Saccharomyces cerevisiae*), mammalian organs (e.g., hog kidney, hog liver, rat liver) and rattlesnake venom.

Yeast cells, such as *Trigonopsis variabilis* (ATCC culture #10679) and the polyploid mutant of the present invention (see Example 1) are particularly useful sources of this enzyme. DAO cleaves the amino group of cephalosporin C.

DAO is located in the microbody and cytoplasm of yeast *Trigonopsis variabilis*. The enzyme can be extracted from the yeast cells by the following procedure: The yeast cell wall is broken open by a high pressure homogenizer, and the clarified cell free extract is treated with an inorganic salt (ammonium sulfate). The ammonium sulfate treated supernatant is fractionated with a chromatographic column containing phenyl Sepharose. This crude enzyme is further purified with mild acid precipitation. At this stage, the specific enzyme activity is approximately 30 units per milligram protein. If further purification is required, an addition chromatographic column containing DEAE functionality may be applied. This enzyme can then be immobilized on to a substrate, such as microporous membrane sheet stock, to form an enzyme reactor.

The enzyme catalase promotes the decomposition of hydrogen peroxide to oxygen and water. However, under high oxygen tension and accompanied with DAO as in the present process, catalase is also a promoter for the oxidative deamination of cephalosporin C to glutaryl 7-ACA. Catalase is an enzyme present in many animal cells. In free solution, the reactivity of the DAO/catalase enzyme mixture increases significantly (at least 180%) compared to DAO alone. With immobilized enzymes (e.g., an enzyme reactor) and under high oxygen tension (e.g., 50 psig), the reactivity increases at least ten to fifteen times.

Surprisingly, when a reactor containing a combination of catalase and D-amino acid oxidase is operated with a high cephalosporin C concentration and under atmospheric pressure without exogenous oxygen diffused into the reaction vessel, the oxygen becomes the limiting factor. Under this circumstance, the reaction becomes reversible and no product is produced. However, when the same reactor is operated under atmospheric pressure with exogenous oxygen diffused into the reactor vessel, the reactivity improved and a small quantity of product is formed. To eliminate the limitation of dissolved oxygen available to the reaction, a pressurized reaction system is employed in the present process. Under this operating condition, the dissolved oxygen is no longer the limiting factor and the reaction becomes dependent on the concentration of its substrate which is cephalosporin C, i.e., the reaction becomes first order. In comparison with atmospheric conditions, the reactivity of the reaction system under about 50 psig pressure increased eight to ten times in the initial production rate and four to five times in the overall reaction rate.

The deacylating enzyme used in the second stage of the present process as an enzyme is expressed in a bacterium, *Acinetobacter sp.* This bacterium is a gram negative small rod of about 0.1×0.3μ in size. Deacylating enzyme, also referred to herein as deacylase, cleaves the glutaryl side chain of the intermediate compound, glutaryl-7 aminocephalosporanic acid (glutaryl 7-ACA).

The deacylating enzyme is located in the cytoplasm of the *A. spp.* gram negative bacterium. Deacylating enzyme can be extracted from the bacterium by the following procedure: A cell paste made from the culture is suspended in a buffer solution containing 0.05M sodium phosphate salt at pH 8.0. The cell wall is broken open by a high pressure homogenizer and the clarified cell free extract is fractioned and concentrated with treatment of ammonium sulfate. The protein concentrate is purified with a liquid chromatographic column containing DEAE. This enzyme is stable for at least six months in frozen condition. This enzyme solution can be immobilized on a substrate, such as silica impregnated microporous plastic sheet (MPS) stock to form an enzyme reactor.

The reaction can be carried out at a pH of from about 7.5 to about 8.5. The optimal pH value for conversion is about 8.5. However, the biological activity of the glutaryl 7ACA and cephalosporin C are more stable below pH 8.0. Thus, pH 8.0 was used in the present process as the operating pH value.

ENZYME-PRODUCING MUTANT CELLS

As stated above, DAO and deacylase are expressed by a number of cells from many different sources. In most cases, however, the levels of the enzymes produced by the cells are too low to be practically useful.

The present invention includes mutant cell lines which are capable of greatly increased expression of DAO and deacylase compared to wild-type cells. These mutant cells were produced by exposing wild-type cells to one or more mutagens under selected conditions and selecting for the surviving cells which showed increased production of the enzymes.

A culture of yeast cells, *Trigonopsis variabilis* (*T. variabilis*) a polyploid mutant, was treated with a nitrosamine compound. The resulting mutant yeast cells produced levels of DAO significantly higher than the wild-type cells.

A culture of *Acinetobacter sp.* (*A. sp.*) cells, which produce deacylase, was treated with a nitrosamine to cause mutation. Mutant strains of *A. sp.* produced in this manner expressed deacylase at significantly higher levels than wild-type *A. sp.*

THE ENZYME REACTORS

The present process is carried out using immobilized enzymes, or enzyme reactors. The enzymes are generally immobilized on a substrate, such as a plastic or cloth support, or, under some conditions, can be free in the reaction solution. Microporous plastic sheets (MPS) are particularly useful supports. However, other support material, such as cotton cloth, can also be used.

Microporous plastic sheet (MPS) is a silica-polyvinylchloride composite in sheet form which can be molded into cartridges of different diameter. MPS can be derivatized with polyethleneimine and glutaraldehyde. The derivatized MPS (PEIGLUT) can react with the amino groups of protein. It has a large surface area per unit weight and can react with protein up to 10% of its own weight.

A polyetheneimine-glutaraldehyde derivatized MPS cartridge (Amerace) is used in the present process for the immobilization of the enzymes. The enzymes, or whole cells which produce the enzymes, can be immobilized on the supports. For example, DAO can be immobilized on the support, or a DAO-producing cell, such as the mutant strain of *Trigonopsis variabilis* described above, can be immobilized, which will produce DAO in the reactor. Approximately 7 grams of protein are immobilized on 100 grams of the activated MPS. To immobilize the enzymes or cells, a solution which contains a buffer, such as 0.05M sodium phosphate salt at a neutral pH, (e.g., pH 6.0) and a specific enzyme or cell suspension, is passed through the activated MPS at 25° C. for two hours or until all of the protein is bound to the MPS, whichever comes first. The MPS is then washed with buffer. The reacted MPS is then washed with a 0.5M glycine solution to cover all of the unreacted aldehyde sites. After further washing with sodium phosphate buffer, the reacted MPS is ready for the enzymatic reaction.

PROCESS STEPS

The process of the invention is carried out in a single reactor vessel. The enzymes are immobilized on the appropriate support, and contacted with a starting material, cephalosporin C.

In a preferred case, a solution of cephalosporin C is used having a concentration of about 1.0 g/liter, and a pH of from about 6.0 to about 8.5. The particularly preferred pH is about 8.0. The cephalosporin C is dissolved in a buffer, such as TRIS buffer. The cephalosporin C solution is first contacted with the immobilized DAO/catalase enzymes, where cephalosporin C becomes oxidized and deaminated, to form glutaryl-7-ACA. The glutaryl 7-ACA product of the first step is then contacted with the second immobilized enzyme, deacylase, which catalyzes its conversion to the desired product 7-ACA. The products of the reaction are 7-ACA, glutaric acid and ammonia.

The reaction is carried out at a temperature of from about 20° to about 50° C., preferably at a temperature of from about 25° C. to about 35° C. The pH range of the reaction can be from about 6.5 to about 9.0, preferably about 8.0. The reaction is carried out under a pressurized oxygen atmosphere, causing oxygen to dissolve in the reaction medium, thereby making it available for the oxidation of cephalosporin C. A pressure, or oxygen tension, of about 50 psig is particularly effective in the present reaction.

In another embodiment of the present invention, sodium borohydride is added to the reaction mixture. Sodium borohydride ($NaBH_4$) increases the half-life of the immobilized DAO enzyme in the reaction.

The present process results in the efficient production of 7-amino cephalosporanic acid in high yield.

Cephalosporins are closely related to penicillin. These compounds are useful as antimicrobial agents for pharmaceutical and medical applications. The present process can be used to produce a cephalosporin derivative, 7-ACA, in high yields which can be the basis for a new series of effective drugs.

7-ACA is a major ingredient, or intermediate, for all the third and fourth cephalosporin family antibiotics including cephalexin, cephaloglycin, cephaloridine, cephalothin, cefaclor, and cephamandole. In the past, most of the 7-ACA production utilized or employed a chemical process using some toxic chemical under an extreme process condition. For the environmental aspects and economical aspects, there is a trend to utilizing a biocatalyst to replace the existing chemical process. In order to produce 7-ACA, the alpha amino adipic acid side chain must be removed from the cephalosporin C molecule. This side chain is too long for most enzymes to react. The present process utilizes a two-step enzymatic process; however, since process conditions are very similar for both enzymes, both steps can be combined in one and becomes a single step process.

The invention is illustrated by the following Examples, which are not to be taken as limiting in any way.

EXAMPLES

Example 1

Polyploid Mutation for *Trigonopsis variabilis*

*Trigonopsis variabilis* polyploid mutant was derived from the wild-type *T. variabilis* as shown in the FIGURE and described below. Wild type cells were treated three times with 0.02% camphor and/or camphor analogues (camphor carboxylic acid and camphor sulfonic acid) for 48 hours. The treated microorganisms were cultivated in YM agar plate for three days at 30° C. A group of fast growing, and also largest in size, single colonies were found. These colonies were then individually treated with N-methyl-N'-nitro-N-Nitrosoguanidine (NTG) for further mutation. 0.25 mg NTG/ml culture was added at a temperature of 0° C., for 40–60 minutes).

A series of *T. variabilis* polyploid mutated single colonies were isolated and cultured. With a combination of modified culture medium and fermentation conditions, the D-amino acid oxidase activity which was expressed in the mutant *Trigonopsis variabilis* were increased from (wild type) 0.1 international unit/ml to 15 international units/ml.

The improved strain of *Trigonopsis variabilis*, designated *T. variabilis* 33187, has been deposited with the American Type Culture Collection, 12301 Parklawn Drive, Rockville, Md. 20852, on Apr. 4, 1989, as ATCC No. 20931.

Culture Method of *Trigonopsis variabilis* (D-Amino Acid Oxidase)

One loop of yeast of *Trigonopsis variabilis* was transferred to a 100 ml culture broth containing: yeast extract, 5 g/l; malt extract; 5 g/l, peptone 5 g/l and glucose 10 g/l (YM medium). The mixture is incubated at 30° C. for 24 hours and transferred to a 500 ml culture flask. The second stage is incubated for 24 hours under the same operating condition as mentioned above. This freshly grown inoculum is then transferred to a fermentation medium which contains solulys, biotin, DL methionine, thiamine, urea and certain inorganic salt. The medium recipe is listed below. The fermenter is maintained at 30° C. for 24 to 48 hours with mild agitation (150–300 rpm) and moderate aeration (0.3 liter/liter/min at arm). The dissolved oxygen is maintained above 50% for the first 12 hours and below 10% thereafter. When the growth reaches stationary phase ($OD_{660}$ reaches 35, pH value of the culture medium is below 5.0 and the cells turn to dark brown), the enzyme expression reached the highest at 36 hours after inoculation. This 60 liter fermentation produced approximately 1730 grams of packed wet cells and 900,000 IUs of D-amino acid oxidase.

| Fermentation medium for *trigonopsis variabilis* | | | |
|---|---|---|---|
| | gm/liter | | gm/liter |
| Medium No. 1 | | | |
| $KH_2PO_4$ | 4 | $MgSO_4.7H_2O$ | 1 |
| $CaCl_2.2H_2O$ | 0.5 | $H_3BO_3$ | 0.1 |
| $(NH_4)_6MoO_{24}$ | 0.04 | $MnSO_4 4H_2O$ | 0.04 |
| $ZnSO_4.7H_2O$ | 0.04 | $CuSO_4.4H_2O$ | 0.045 |
| $FeSO_4.7H_2O$ | 0.025 | DL Methionine | 2.67 |
| Biotin | 0.02 | Thiamine | 0.0001 |
| Glucose | 20 | urea | 2.5 |
| Mazu df 285 (antifoam) | 1 ml | | |
| Medium No 2 | | | |
| $KH_2PO_4$ | 4 | Urea | 1 |
| $MgSO_4.7H_2O$ | 1 | DL Methioine | 3 |
| Solulys | 7.5 | Biotin | 0.02 |
| Glucose | 15 | sucrose | 10 |
| Mazu df 285 (antifoam) | 1 ml | | | pH adjusted to 5.6 before sterilization

Example 2

Isolation and Purification of D-Amino Acid Oxidase 1730 grams of cells prepared as described in Example 1 were resuspended in 7.7 liters of 0.01M of pyrophosphate, 0.01 EDTA at pH 8.0. The cell suspension was passed through a high pressure homogenizer (manton-Gaulin homogenizer @11,000 psi) three times. At this stage, 260,000 units of D-amino acid oxidase were recovered. The clarified supernatant (9.3 liters) was then mixed with 1553 grams of ammonium sulfate for about 60 to 90 minutes. A Sharples centrifuge separated the precipitate and supernatant. The clarified supernatant (9.3 liters) was put onto a phenyl Sepharose liquid chromatographic column which was equilibrated with 1.2M ammonium sulfate. The enzyme was eluted with 0.01M pryophosphate buffer with 0.001M EDTA at pH 8.3. The result: 58.5% of the enzyme activity was recovered. The pooled fraction then treated with acetic acid to pH 5.2. The recovered enzyme had a specific activity of 30 units per milligram protein. Approximately 95,000 IU of D-amino acid oxidase were recovered. The enzyme was stored at 4° C. with DTT (5 mg/ml) and was stable for two weeks until immobilization.

Example 3

Mutation of *Acinetobacter sp.*

A wild type gram negative bacteria, *Acinetobacter sp.* (*A. sp.*), utilizes glutaric acid as its sole carbon source and produces 0.005 to 0.01 international units of deacylase per milliliter.

The bacteria was treated with N-methyl-N'-nitro-N-nitrosoguanidine (NTG) and ethylmethanesulfonate. The conditions of this treatment were 0.2 to 0.5 mg/ml at 0° C. for 10 to 50 minutes. The enzyme deacylase activity was increased from (wild-type) 0.005–0.01 IUs/ml to 0.4 IUs/ml.

The improved strain of *A. sp.* designated *A. sp.* YS114, has been deposited with the American Type Culture Collection, 12301 Parklawn Drive, Rockville, Md. 20852, on Apr. 4, 1989 as ATCC No. 53891.

Culture of Deacylating Enzyme Producing Bacterium

A single colony of YS114 strain was transferred to 100 ml of culture medium at 25° C. for 24 hours. The inoculum medium formula is listed below:

The formula of inoculum culture medium for YS114, (YM medium)

| Becto Peptone | 10 g/l |
| yeast extract | 2 g/l |
| beef extract | 5 g/l |
| NaCl | 5 g/l |
| glutaric acid | 1 g/l at pH 7.0 |

The fermentation medium formula is listed below:
The formula of fermentation medium for YS114

| Medium No. 1 | |
| --- | --- |
| proflo | 10 g/l |
| yeast extract | 5 g/l |
| solulys | 2 g/l |
| glutaric acid | 1 g/l |
| NaCl | 5 g/l |
| glucose | 10 g/l at pH 7.5 |
| Medium No. 2 | |
| yeast extract | 2 g/l |
| $KH_2PO_4$ | 1 g/l |
| solulys | 2 g/l |
| Mono sodium glutamate | 2 g/l |
| NaCl | 5 g/l |
| Atgel 200 | 20 gl at pH 7.5 |

A 550 liter fermenter was used for the enzyme production. A 10 liters inoculum was used and the fermentation was operated at 25° C. with moderate air (21/1/m) and high agitation (400–600 rpm). The dissolved oxygen levels was maintained at or above 50% of saturation, pH was not controlled throughout the run, the pH value eventually rose to 8.5. The culture was fermented for 30 hours and the enzyme expression attained 400 international units per liter of broth. Approximately 2527 international units of enzyme and 5500 grams of cell paste were recovered from a sharples centrifuge.

*Internationa unit (IU)—one micromole of 7 ACA produced per min at 37° C. at pH 8.0

Example 4

Isolation and Purification of Deacylating Enzyme 2.6 kilograms of packed *A. sp.* cells prepared as described in Example 3 were thawed at room temperature overnight and suspended in 2.6 liters of 0.1M sodium phosphate buffer pH 8.0. The suspension was mixed with an additional 6 liters of buffer, and passed through the high pressure homogenizer three times, and a clarified supernatant was recovered. At this stage, 11.5 liters and 1132 IUs of deacylating enzyme activity were recovered. 1171 grams of ammonium sulfate were added to the solution, mixed for 60 minutes, and centrifuged with a Sharples centrifuge. The supernatant and an additional 2021 grams of ammonium sulfate were added. After centrifugation, 522 units of enzyme were recovered. This protein precipitate was dissolved in 0.05M sodium phosphate buffer at pH 8.0 and dialysed with the same buffer overnight. The enzyme solution was then fractionated with a DEAE liquid chromatographic column and eluted with a 0 to 0.3M NaCl linear concentration gradient. The enzyme peak was eluted at 0.1M NaCl salt. At this stage, 4.7 grams and 426 international units (0.089 IUs/mg protein) of deacylating enzyme were recovered. The enzyme was stored frozen at −20° C. and was ready for immobilization. This preparation was stable for six months.

Example 5

Enzyme Immobilization

Immobilization Method for D-Amino Acid Oxidase 300 ml of D-amino acid oxidase (DAO) solution (7140 IU, 900 mg) were passed through a 0.5 inches thick (23 sheets @47 mm in diameter) activated MPS. The DAO solution was recycled at 6 ml/min for 2 hours. 90% of the enzyme was attached to MPS. The excess aldehyde sites of the reactor were quenched with 0.5M glycine in 0.05M TRIS buffer pH 8.0 and was stored in 0.05M TRIS buffer at 4° C. This reactor was subsequently used for ceph C/glutaryl-7-ACA conversion study.

Immobilization Method for D-Amino Acid Oxidase and Catalase 770 milligrams of DAO (30 IU/mg from ex 1481 and 5 mg/ml DTT) and 10.2 mg catalase (sigma C30, 22,800 IU/mg) were immobilized on 9600 mg (0.5 inches thick, 24 sheet 47 mm in diameter) of PEI/GLU activated MPS. The enzyme solution was passed through the reactor three times at 6 ml/min. The excess aldehyde sites of the reactor were quenched with additional 300 ml of 0.5M glycine in 0.05M TRIS buffer at pH 8.0. The reactor was then washed with 0.05M TRIS buffer at pH 8.0 and stored in 20 ml of same buffer containing 10 μg/ml of gentamycin. The efficiency of immobilization was approximately 89% with a total of 20670 units of D-amino acid oxidase immobilized onto the reactor (860 units of D-amino acid oxidase per sheet of MPS).

Immobilization Method of Enzyme 2-Deacylating Enzyme

A PEI/GLU activated module with 12 sheets of MPS (47 mm diameter and 4800 mg) was used. 110 milliliters of enzyme II solution (0.2 international units/ml, 22.2 units and 392 mg protein) was passed through the reactor three times at 6 ml/min. The reactor was washed with 200 ml of 0.5M glycine in 0.05M TRIS buffer at pH 8.0, followed by flushing with 100 ml of 0.05M TRIS buffer. After washing, the reactor was stored in 0.05M TRIS buffer at pH 8.0 with 10 μg/ml gentamycin. In result, a total of 331 mg of protein and 19 international units was attached onto the reactor. 84.5% of enzyme 2-deacylating enzyme was attached (1.56 IUs per sheets of MPS).

Example 6

Effect of pH, Temperature and Pressure on Enzyme Activity

Effect of pH of Cephalosporin C vs the Reactivity of Immobilized Enzymes D-Amino Acid Oxidase/Catalase The effect of pH on D-amino acid oxidase/catalase enzyme mixture was studied using a cephalosporin C solution with a concentration of 1.0 grams/liter. A stock solution was made and 100 ml aliquots were divided and pH was adjusted to 6,0, 7.0 and 8.0. Each aliquot of cephalosporin C solution was passed through the reactor containing the immobilized enzymes in a single pass mode at a rate of 2 ml/min. The reactor was flushed with the appropriate buffer solution prior to the experiment. These experiments were run at room temperature and at atmospheric pressure. The optimal pH is at 8.0.

TABLE I

| pH | RELATIVE REACTIVITY |
| --- | --- |
| 6.0 | 75% |
| 7.0 | 85% |
| 8.0 | 100% |

Effect of Operating Temperature vs Reactivity of Immobilized Enzyme D-Amino Acid Oxidase The effect of temperature on D-amino acid oxidase was studied at several operating temperature conditions. The reactor was operated in a water bath which is set at 20°, 25°, 30°, 35°, 40°, 45° and 50° C. The operating parameter run at 2 ml/min, pH 8.0 with a cephalosporin C concentration of 1 gm/liter. The reactivity reached its maximum at 45° C., however, the reactor has a similar performance between 30° and 45° C. The results from the temperature study are shown in Table II:

TABLE II

| TEMPERATURE °C. | % RELATIVE REACTIVITY |
| --- | --- |
| 20 | 65 |
| 30 | 92 |
| 35 | 94 |
| 40 | 95 |
| 45 | 100 |
| 50 | 82 |

Effect of Substrate pH vs the Reactivity of Immobilized Enzyme Deacylase

The effect of pH on deacylase was studied using a dilute substrate, single pass mode of approach. A stock solution of 5.55 g/l of glutaryl 7-ACA was made and 100 ml aliquots were divided and pH adjusted with 1N NaOH to the following values: pH 5.0, 7.0, 7.5, 8.0, 8.5 and 9.0. Each aliquot of substrate was then pumped through an enzyme II reactor in single pass mode at a rate of 2 ml/min with a peristaltic pump. The experiment was run at room temperature and at atmospheric pressure.

As it can be seen, the optimal pH for the conversion of glutaryl 7ACA to 7ACA by using enzyme II is approximately 8.5. The relative reactivities at various pH levels are shown in Table III:

TABLE III

| pH | RELATIVE REACTIVITY |
| --- | --- |
| 5.0 | 57% |
| 7.0 | 58% |
| 7.5 | 66% |
| 8.0 | 76% |
| 8.5 | 100% |
| 9.0 | 98% |

Effect of Operating Temperature vs Reactivity of Immobilized Enzyme D-Amino Acid Oxidase The effect of temperature on reactor II was studied at several operating temperature conditions. The reactor was operated in a water bath which is set at 20°, 25°, 30°, 35°, 40°, 45°, 50°, 55° and 60° C. The operating parameter was set at 2 ml/min pH 8.0 with a concentration of glutaryl 7ACA at 0.45 gm/liter. The reactivity reached its maximum at 45° C., however, the reactor has a similar performance between 35° and 45° C. The result from the temperature study is shown in Table IV:

TABLE IV

| TEMPERATURE °C. | % RELATIVE REACTIVITY |
| --- | --- |
| 20 | 73 |
| 25 | 75 |
| 30 | 83 |
| 35 | 92 |
| 40 | 97 |
| 45 | 100 |
| 50 | 87 |
| 55 | 84 |
| 60 | 62 |

Oxygen Tension vs Reactivity of Both Enzyme Reactors

This experiment demonstrated the effectiveness of dissolved oxygen in the de-amination reaction of cephalosporin C to glutaryl 7-ACA. The reactor was operated under a 50 psig pressure with pure oxygen diffused into the reaction vessel. The cephalosporin C solution, 51.3 to 64.5 g/l in concentration, pH 8.0, was pumped through the reactor in a recycled mode. This reactor demonstrated a high initial reaction rate of 19.6 gm of glutaryl 7-ACA produced per minute per sheet of reactor and overall rate of 8.4. Compared with the reaction operated at atmospheric pressure with pure oxygen diffused into reaction vessel, the reaction rate reduced to a range between 1.7 to 2.3 gm of glutaryl 7-ACA produced per minute per sheet of reactor. The reactivity was similar between the initial and overall production rate. The comparison of these studies is listed in the chart shown as below. Furthermore, not only the reactivity was improved significantly, the reaction product also improved to the extent that glutaryl 7-ACA becomes the dominant product, as shown in Table V:

TABLE V

| TIME | RATE (mg glutaryl7ACA produced/min/sheet of MPS) | | |
|---|---|---|---|
| Minutes | 50 psig[1] | 0 psig[2] | 0 psig[3] |
| 20 | 19.6 | n.d. | n.d. |
| 40 | 13.4 | n.d. | n.d. |
| 60 | 11.3 | 2.6 | 1.55 |
| 80 | 8.4 | n.d. | n.d. |
| 90 | n.d. | 2.6 | n.d. |
| 120 | n.d. | 2.65 | 1.60 |
| 180 | n.d. | n.d. | 1.75 |

[1]Operated at 50 psig, pH 8.0 and flow rate of 6 ml/min. 24 sheets reactor.
[2]Operated at atmospheric pressure, pH 8.0 and 6 ml/min. One sheet reactor.
[3]Operated at atmospheric pressure, pH 8.0 and 14 ml/min. 4 sheets reactor.

Example 7

Condition and Result of Enzyme Reactor of D-Amino Acid Oxidase/Catalase, Under 50 Psig Oxygen Tension 19.35 grams of purified cephalosporin C (Lot number 235CX6) were dissolved in 300 ml of 0.15M TRIS buffer and pH was adjusted to 8.0 with 0.1N NaOH. Cephalosporin C solution was pumped through enzyme reactor (DAO/catalase) and recycled at 6.0 milliliters per minute. The whole system was under a 50 psig pressure pure oxygen enriched environment. Within 80 minutes, all of cephalosporin C was converted to 8-keto acid (14.88 gm/l) and glutaryl 7-ACA (52.6 gm/l). A production rate of 197 mg glutaryl 7-ACA per minutes (8.2 mg/min/sheet of reactor) with a 90.6% of product recovery (molar ratio) was achieved. Under the oxygen enriched environment, the oxygen becomes abundant, this reaction becomes first order. The results are shown in Table VI:

TABLE VI

| REACTOR ONE UNDER 50 PSIG OXYGEN PRESSURE | | | | | | |
|---|---|---|---|---|---|---|
| TIME Minutes | pH | CEPH C g/l | CEPH C utilized g/l | α keto g/l | GL7ACA g/l | MOLAR RECOVERY |
| 0 | 8.0 | 64.5 | 0 | 0 | 0 | |
| 20 | 7.7 | 28.3 | 36.2 | 14.3 | 31.4 | 96.4% |
| 40 | 7.3 | 12.3 | 52.2 | 14.2 | 42.8 | 91.3% |
| 60 | 7.25 | 4.3 | 60.2 | 14.6 | 54.4 | 93.7 |
| 80 | 7.1 | 0.0 | 64.5 | 14.8 | 52.6 | 90.6% |

Condition and Result of Enzyme Reactor of D-Amino Acid Oxidase, Under Atmospheric Oxygen Pressure 2.04 grams of purified ceph C (Lot number 234CX6) were dissolved in 50 ml of 0.15M TRIS buffer, pH 8.0. The pH of dissolved ceph C solution was adjusted to 6.7 with 0.1N NaOH. Ceph C solution was pumped through enzyme reactor I at 10.0 milliliter per minute while pure oxygen is bubbling through a sparger into the reaction reservoir. Under this low oxygen tension, the reactivity of the reactor was about one fifth of the reactivity under high oxygen tension at 50 psig as listed in Example 7. The production of this experiment is approximately 6.4 mg glutryl 7ACA per minutes (1.6 mg per minutes per sheet of reactor) with a product recovery (molar) of 78.0%, as shown in Table VII:

TABLE VII

| ATMOPHERIC OXYGEN PRESSURE | | | | | |
|---|---|---|---|---|---|
| TIME minutes | ceph C g/l | ceoh C utilized g/l | α keto g/l | GL7ACA g/l | molar recovery |
| 0 | 40.1 | 0 | 0 | 0 | |
| 30 | 33.2 | 6.9 | 3.2 | 3.6 | |
| 60 | 23.8 | 16.3 | 6.2 | 7.4 | |
| 120 | 17.1 | 23.0 | 12.0 | 15.3 | |
| 180 | 5.5 | 34.6 | 20.2 | 25.2 | 80.9% |
| 210 | 1.9 | 38.2 | 17.4 | 26.8 | 78.0% |

Condition of Chemical Reaction for Glutaryl 7-ACA 6.0 milliliters of 3.0% hydrogen peroxide solution were added to the product solution from the previous experiment (a mixture of δ-keto intermediate and glutaryl 7ACA) for two hours at 25° C. All the δ-keto acid converted to glutaryl 7-ACA. A final glutaryl 7ACA concentration was analyzed to be 25.9 grams per liter.

Condition and Result of Enzymatic Reaction for Deacylase 115 ml of glutaryl 7ACA solution (25.9 gm/l, 3 grams) was passed through to enzyme reactor II (deacylase immobilization 35 sheets of MPS @47 mm in diameter) at a flow rate of 6 milliliters per minute. The pH of the substrate was adjusted to 8.0 manually. The reaction was run for four (4) hours with a production rate of 5.8 mg of 7-ACA per minute. 1.4 grams of 7-ACA was recovered after the reaction terminated. The molar product recovery of this reactor was 75 to 83%.

Example 8

Single Step Conversion of Cephalosporin C to 7ACA

A single step conversion of Cephalosporin C to 7ACA was achieved using the following enzyme reactor configuration. An enzyme 1 reactor (5 sheets of 47 mm diameter containing a total of 3450 units D-amino oxidase) was followed immediately downstream by an enzyme 2 reactor composite (24 sheets of 47 mm diameter containing a total of 31 international units deacylating enzyme). 300 ml of ceph C solution, 6.6 g/l in 0.1M TRIS pH 8.0, recycled through this system at a rate of 4.4 ml/minute. The entire system was pressurized under 50 psig oxygen. The results are shown in Table VIII:

TABLE VIII

| Time (min) | Ceph C (g/l) | alpha-keto (g/l) | GL7ACA (g/l) | 7ACA (g/l) |
|---|---|---|---|---|
| 0 | 6.6 | 0 | 0 | 0 |
| 30 | 6.3 | 0 | 0 | 0.03 |
| 60 | 5.36 | 0 | 0.07 | 0.11 |
| 90 | 4.15 | 0 | 0.18 | 0.23 |
| 120 | 3.94 | 0 | 0.30 | 0.37 |

TABLE VIII-continued

| Time (min) | Ceph C (g/l) | alpha-keto (g/l) | GL7ACA (g/l) | 7ACA (g/l) |
|---|---|---|---|---|
| 180 | 2.85 | 0 | 0.46 | 0.70 |
| 240 | 1.97 | 0 | 0.50 | 1.0 |
| 300 | 1.85 | 0 | 0.51 | 1.53 |
| 360 | 1.45 | 0 | 0.41 | 1.70 |
| 420 | 0.90 | 0 | 0.29 | 1.80 |
| 465 | 0.75 | 0 | 0.23 | 1.89 |

After the substrate was recycled for 7.75 hours, the substrate was removed. The reactor was flushed with 95 ml of TRIS buffer 0.05M pH 8.0. A total of 10.45 mg Ceph C, 30.4 mg glutaryl 7-ACA, and 123.5 mg 7-ACA were recovered. The overall production rate of 7-ACA was 1.49 mg/min with an overall recovery of 62.9%. No alpha-keto intermediate was detected.

Example 9

Effect of Sodium Borohydride on Reactor Life of D-Amino Acid Oxidase

Bond stabilization between the enzyme and support was attempted by using a treatment of glutaraldehyde followed by sodium borohydride. Glutaraldehyde was used to attach enzyme to any possible pendant PEI group. Sodium borohydride was used to reduce Schiff bases formed by the aldehyde-to-amino linkage, thereby, saturating the bond and protecting it from attack.

|  | #1765B untreated | #1816C Glu—NaBH$_4$ |
|---|---|---|
| Projected half life | 12 hours | 130 hours |
| Glutaryl-7ACA made mg/IU in first ½ life | 5.8 mg/IU | 44 mg/IU |

Example 10

Deacylase Glutaraldehyde Fixed Cells

To 10 grams of *Acinetobacter sp.* cell paste (20 hours harvest) 80 ml of pH 8.6 saline was added. Then 25% glutaraldehyde was added to the solution to make a final concentration of 1%. pH was adjusted to 6.5 and the mixture was allowed to sit or stirred slowly at room temperature for one hour. The cells were spun down and washed twice with 0.1M phosphate buffer and resuspended in the same buffer. Before fixation the enzyme activity was 726.5 IU/ml; after fixation the activity was 704.5 IU/ml, showing a 3% loss in activity.

Cells suspended in 80 mls. of glutaryl-7ACA solution (35 g/l pH 8.0). The pH was adjusted to pH 8.0 periodically with 10N NaOH.

Projected half life is 170 hours (based on assayed activity of cells).

Total 7ACA made during the first half life of reactor 5.95 grams.

Average rate is 0.516 mg/hr IU.

7ACA made mg/IU in first half life equals 104 mg/IU.

Example 11

Immobilized *T. Variabilis* Cells on Cotton Cloth

Two samples of *T. variabilis* 33187 were treated as follows: 25 grams of cell paste with 3% ethyl acetate for 20 minutes. The cell mixture was spun down and the supernatant was removed. Both samples were resuspended in 100 mls. each of 0.05M phosphate buffer, pH 8.0. The samples were passed once through a 4.9 gram stack of polyethyleneimine glutaraldehyde derivatized flannel, 47 mm×½" thick, packed into the reactor cartridge shell, and fixed with 2% glutaraldehyde for 2 hours. The samples were then flushed with the same buffer. The binding capacity was 4.5 g of whole cell and 10 g of minus-extract cell. Testing conditions were 50 psig $O_2$, 22 ml/min flow rate and cephalosporin C concentration 40 g/l. Results are as follows:

|  | Whole cell | Minus-extract cell |
|---|---|---|
| Projected half life | 200 hrs. | 465 hrs. |
| Glutaryl-7ACA made during first ½ life | 5.2 gm/gm cell | 8.24 gm/gm cell |
| Ave. rate when new | 1.3 mg/min gm | 1.4 mg/min gm |

A life study was run with a pair of D-amino acid oxidase reactors at 40 grams/liter Cephalosporin C at 50 psig $O_2$ and 22 ml/min flow rate. Reactors were run overnight in a batch recycle mode and washed with an FAD-Mercaptoethanol reducing cocktail every 24 hours.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

We claim:

1. A process for producing 7-amino cephalosporanic acid comprising the steps of:
    (a) contacting cephalosporin C with catalase and with D-amino acid oxidase obtained from *T. variabilis* strain ATCC 20931, in a reaction vessel having externally supplied oxygen to cause deamination of cephalosporin C, thereby forming glutaryl 7-amino cephalosporanic acid;
    (b) contacting the product of step (a) with a deacylase enzyme obtained from *Acinetobacter sp.* strain ATCC 53891, said deacylase enzyme being specific for the glutaryl side-chain of glutaryl 7-amino cephalosporanic acid under conditions sufficient to produce 7-amino cephalosporanic acid; and
    (c) recovering said 7-amino cephalosporanic acid.

2. The process of claim 1, wherein the D-amino acid oxidase and the catalase are immobilized on a support.

3. The process of claim 1, wherein the deacylase is immobilized on a support.

4. The process of claim 1, wherein said deamination of cephalosporin C occurs at a temperature range of from about 20° C. to about 45° C., a pH of from about 6.5 to about 8.5, and an oxygen pressure of about 50 psig.

5. The process of claim 4, wherein the temperature is from about 25° C. to about 35° C., the pH is 8.0, and the oxygen pressure is about 50 psig.

6. A process for producing 7-amino cephalosporanic acid comprising:

(a) combining in a reaction vessel cephalosporin C, catalase, D-amino acid oxidase obtained from *T. variabilis* strain ATCC 20931, externally supplied oxygen, and deacylase obtained from *Acinetobacter sp.* strain ATCC 53891 under conditions sufficient to produce 7-amino cephalosporanic acid; and (c) recovering said 7-amino cephalosporanic acid.

7. The process of claim 6, wherein the reaction vessel is pressurized.

8. The process of claim 6 wherein said D-amino oxidase is immobilized on a solid substrate derivatized with polyethyleneimine and glutaraldehyde, the immobilization procedure including the addition of sodium borohydride to reduce Schiff bases that form as said D-amino acid oxidase is bonded to said derivatized solid substrate.

* * * * *

UNITED STATES PATENT AND TRADEMARK OFFICE
CERTIFICATE OF CORRECTION

PATENT NO. : 5,618,687
DATED : April 8, 1997
INVENTOR(S) : Bing L. Wong and Yong Qiang Shen It is certified that error appears in the above-identified patent and that said Letters Patent is hereby corrected as shown below:

On the Title page, item [54] and in Col. 1, the title should read

--PRODUCTION OF 7-AMINO CEPHALOSPORANIC ACID WITH
D-AMINO ACID OXIDASE AND DEACYLASE--

Signed and Sealed this

Seventeenth Day of February, 1998

Attest:

BRUCE LEHMAN

*Attesting Officer*      *Commissioner of Patents and Trademarks*